United States Patent [19]

Rauterkus et al.

[11] Patent Number: 5,307,794

[45] Date of Patent: May 3, 1994

[54] OSCILLATING VENTILATOR APPARATUS AND METHOD AND PATIENT ISOLATION APPARATUS

[75] Inventors: L. Thomas Rauterkus; Samuel B. Cowan, both of Yorba Linda, Calif.

[73] Assignee: Sensormedics Corporation, Yorba Linda, Calif.

[21] Appl. No.: 857,604

[22] Filed: Apr. 1, 1992

[51] Int. Cl.$^5$ .............................................. A61M 16/00
[52] U.S. Cl. ........................... 128/204.18; 128/200.24; 128/202.27; 128/917; 128/909; 128/204.25
[58] Field of Search ................... 137/505.36; 446/416; 181/148, 161; 403/31, 50, 51; 128/200.24, 202.27, 205.18, 204.25, 205.24, 204.21, 205.13, 204.18, 917, 918, 909

[56] References Cited

U.S. PATENT DOCUMENTS

| | | | |
|---|---|---|---|
| 705,398 | 7/1902 | Gustine | 446/416 |
| 2,762,164 | 9/1956 | Hester | 446/416 |
| 2,918,917 | 12/1959 | Emerson | 128/204.21 |
| 4,719,910 | 1/1988 | Jensen | 128/204.21 |
| 4,747,402 | 5/1988 | Reese et al. | 128/204.21 |
| 4,805,612 | 2/1989 | Jensen | 128/204.21 |
| 4,821,709 | 4/1989 | Jensen | 128/204.21 |
| 5,092,326 | 3/1992 | Winn | 128/205.13 |
| 5,165,398 | 11/1992 | Bird | 128/204.25 |

FOREIGN PATENT DOCUMENTS 462412 12/1991 European Pat. Off. .
1263253 6/1984 U.S.S.R. .

Primary Examiner—Edgar S. Burr
Assistant Examiner—Eric P. Raciti
Attorney, Agent, or Firm—Lyon & Lyon

[57] ABSTRACT

An apparatus and method for facilitating the transfer of an oscillating ventilator apparatus from one patient to the next, without requiring disinfection of the air pulse generating diaphragm and components, by separating the airway of the patient from the air pulse generating apparatus by a patient isolation apparatus comprising a patient isolation connection unit which mounts a flexible, fluid-impervious diaphragm in sealing relation to the ventilator housing and in adjacent relationship to the outer face of the air pulse generating apparatus, whereby no fluids emanating from the patient can contact said air pulse generating apparatus. The patient isolation apparatus may be disposed of after use with one patient, or may be disinfected and reused.

13 Claims, 4 Drawing Sheets

OSCILLATING VENTILATOR APPARATUS AND METHOD AND PATIENT ISOLATION APPARATUS

BACKGROUND OF THE INVENTION

The invention relates generally to ventilators for supporting ventilation in air breathing mammals, both humans and animals. More particularly, the present invention relates to high frequency ventilators which operate by supplying oscillating respiratory gases to a patient at a frequency above the normal breathing frequency of the patient.

High frequency oscillating ventilators are well known and have been previously described in, e.g., U.S. Pat. No. 4,719,910, which is incorporated hereby by reference in its entirety. Unlike conventional ventilators which ventilate by positive-pressured gas flow and rely on passive recoil of the lung tissue for expiration, high frequency oscillating ventilators employ an active expiratory phase in which gas is pushed into and pulled out of a patient's lungs during alternate half-cycles of the oscillating diaphragm (or piston) of the ventilator. The forward motion of the diaphragm (toward the patient) creates a positive-going pressure relative to the static pressure in the patient's airway. As the diaphragm is driven rearward from its most forward position, the dynamic pressure it generates reverses from positive-going to negative-going. This bipolar dynamic pressure waveform is the principle reason for the success of the high frequency oscillating ventilator in providing improved respiratory gas exchange.

A problem that has been encountered in the use of high frequency oscillating ventilators of the type disclosed in the aforesaid U.S. Pat. No. 4,719,910 is that gases, vapors, and secretions, in other words, fluids, from the lungs and airways of a patient return with the expired air, and may contaminate all parts of the oscillating ventilating machine which they directly contact or to which they may migrate. While patient endotracheal tubes and associated parts and connections used for the introduction of gas, anesthetics, medications, etc. to a patient are generally disposed of when transferring the high frequency oscillating ventilator from one patient to another, the vibrator unit, which produces the oscillating pulses of air or oxygen, cannot be disposed of because of the relatively high cost of manufacture of such units. Therefore, in order to avoid cross-contamination or cross-infection between patients, time consuming and rigorous cleaning and disinfection procedures have been a necessary and expensive step preceding the transfer of the high frequency oscillating ventilation machine from one patient to another.

SUMMARY OF THE INVENTION

A high frequency oscillating ventilator embodying or utilizing this invention incorporates a construction wherein the air pulse generating portions of the ventilation machine, and particularly the vibrating diaphragmatically sealed piston, are isolated from any contact whatsoever with patient fluids. The housing which mounts the electrically actuated mechanism for producing the desired gas pressure pulses has an open end which is sealably closed by a diaphragmatic piston which has its periphery sealably closing the open end of the housing. The piston is vibrated at a selected frequency and in accordance with a selected wave form in the same manner as described in the aforementioned U.S. Pat. No. 4,719,910. The external face of the piston, however, does not come in contact with any patient fluids or with any apparatus which is exposed to patient fluids. This is accomplished by providing a patient isolation apparatus which is in communication with the diaphragmatically sealed piston but which is impenetrable to such patient fluids and prevents contact by such fluids with the piston face. The patient isolation apparatus comprises a flexible diaphragm sealed to a patient connection unit.

In the preferred embodiment, the patient isolation connection unit comprises a frusto-conical shaped annular connecting element having a large end defining a peripheral rim portion and a small end defining a tubing connection for connecting to tubing leading to the airway of a patient. A flexible diaphragm disc is provided having a peripheral portion sealably secured to the large end of the frusto-conical shaped annular element. Such annular element is then detachably secured to the peripheral end face of the housing so as to dispose the medial portion of the flexible diaphragm disc in parallel, closely spaced relationship to the diaphragmatically sealed piston. Preferably, the diaphragmatically sealed piston is in contact with the flexible diaphragm disc and moves in tandem with it. Thus, the vibrations of the diaphragmatically sealed piston are directly transmitted to the flexible diaphragm disc. If not in direct contact, the vibrations of the diaphragmatically sealed piston produce sufficient compression of the limited quantity of air disposed between such piston and the flexible diaphragm disc to cause compression waves in such air which set the diaphragm disc into vibration in synchronism with the diaphragmatically sealed piston.

In a preferred embodiment of the invention, the periphery of the flexible diaphragm disc is utilized as a gasket between the patient isolation apparatus and the housing end face. A plurality of quick release clamps are mounted on the end face of the housing in peripherally spaced relationship and are movable into clamping relationship with respect to the peripheral rim portion of the patient isolation apparatus by a small (approximately 90°) turning movement of the clamps. Other mounting or clamping mechanisms may also be utilized.

In accordance with this invention, the patient isolation connection unit and its attached flexible diaphragm disc, as well as all tubing connecting the connection unit to the patient's airways, can be fabricated from a relatively inexpensive plastic material, thus making the cost of the items sufficiently low that they can be disposed of after each use. Alternately, these items can be disengaged from the oscillating ventilator housing and disinfected separately.

To transfer the high frequency oscillating ventilator apparatus to the next patient, it is only necessary to remove the patient isolation apparatus or assembly (e.g., the patient isolation connection unit and its attached flexible diaphragm disc) from the ventilator housing utilizing the quick release clamps, and to replace it with a replacement patient isolation assembly. Thus, no portion of the high frequency oscillating ventilating machine which generates the air pulses having the desired wave form and frequency are ever placed in contact with patient fluids, while at the same time eliminating the sterilization time and costs required for components of the prior art construction of high frequency oscillating ventilators. The cost of a disposable patient isolation assembly fabricated in accordance with this invention is substantially less than the costs incurred to disinfect the prior art construction. Utilization of such patient isolation assembly also permits shift of the high frequency oscillating ventilator machine to use for another patient with minimal delay time.

Further objects and advantages of this invention will be readily apparent to those skilled in the art from the following detailed description, taken in conjunction with the annexed sheets of drawings, on which is shown a preferred embodiment of the invention.

DETAILED DESCRIPTION

Figure 1:
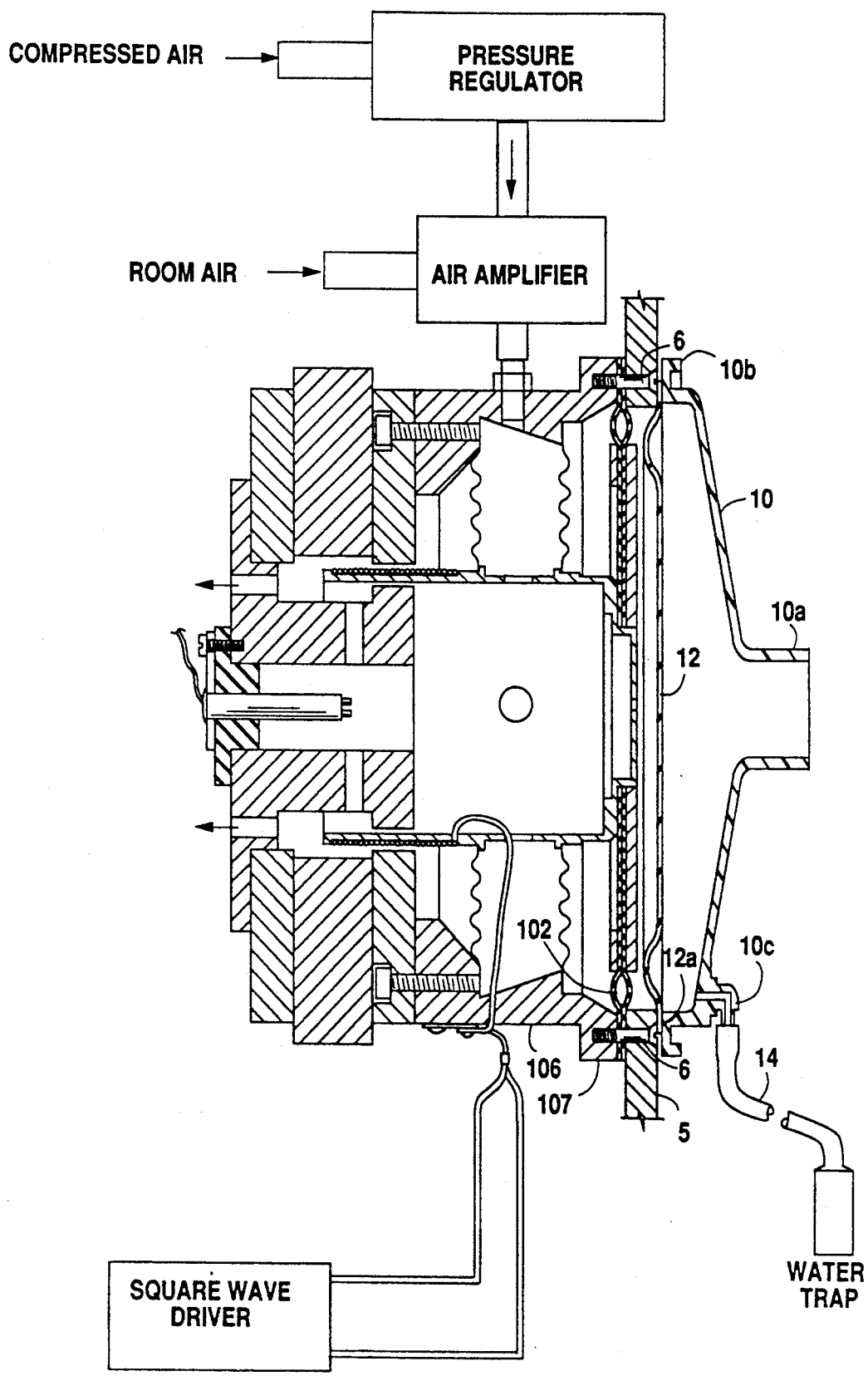
FIG. 1 is a schematic vertical sectional view illustrating an assemblage of major components for a high frequency oscillating ventilator, including a patient isolation apparatus embodying this invention.
Figure 2:
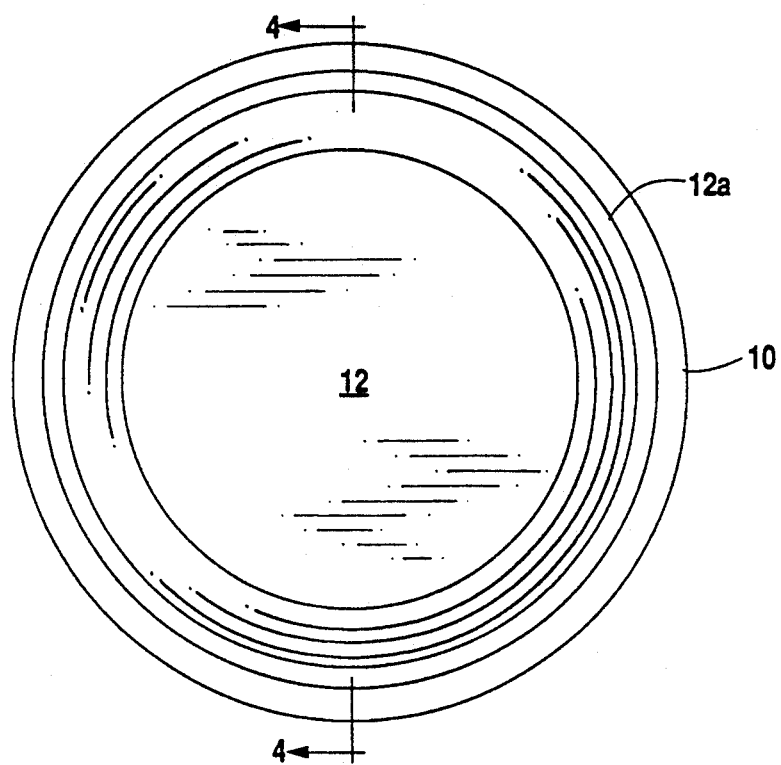
FIG. 2 is a front elevation view of a patient isolation apparatus for a high frequency oscillating ventilator embodying this invention.
Figure 3:
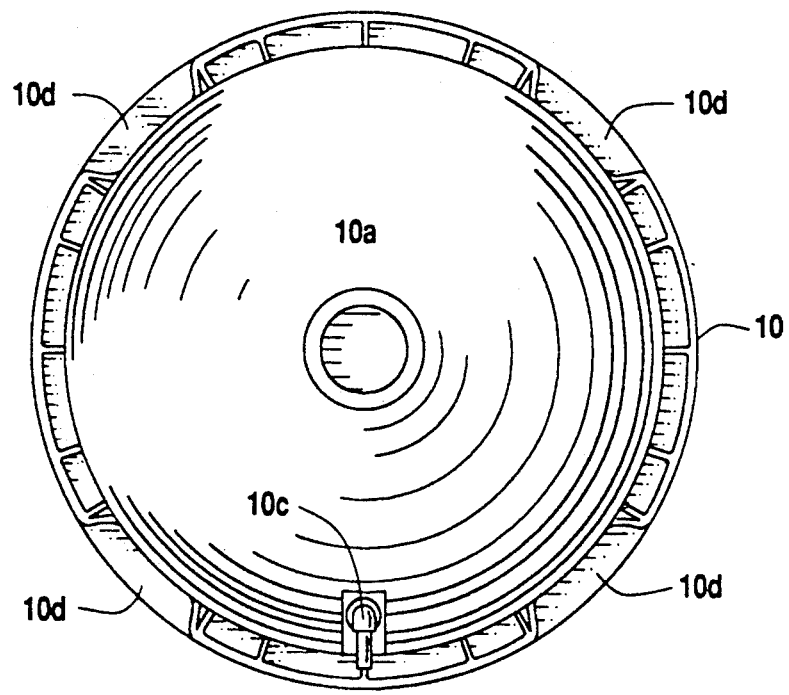
FIG. 3 is a rear view of the patient isolation apparatus.
Figure 4:
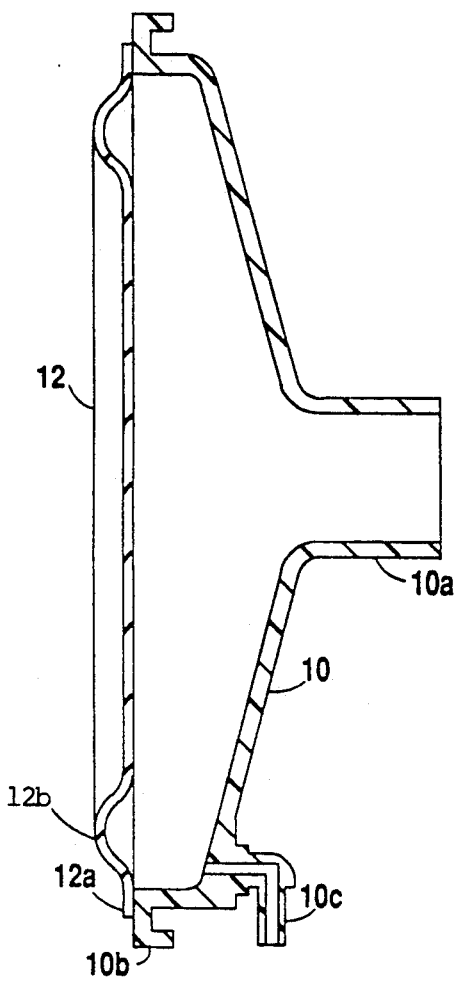
FIG. 4 is a vertical section view taken on the plane 4—4 of FIG. 2.

Referring to FIG. 1, there is schematically shown all of the elements commonly used in a high frequency oscillating ventilator apparatus of the type described in U.S. Pat. No. 4,719,910, but incorporating the current invention. The conventional portions of the apparatus will therefore be mentioned only from the standpoint of their relationship to the current invention.

Thus, on the right hand side of the apparatus as viewed in FIG. 1, a diaphragmatically sealed piston 102 has its periphery sealingly secured between a back plate 5 and a peripheral flange 107 of an annular housing element 106 by a plurality of bolts 6. The patient isolation connection unit 10 is preferably fabricated by injection molding of a suitable plastic, such as that sold under the trademark CYROLITE plastic molding compound Oyrolite. The patient isolation connection unit 10 is preferably of generally frusto-conical shaped configuration, having at its small end a cylindrical protuberance 10a to which a plastic tube (not shown) leading to the patient may be conventionally secured. The large end of the patient isolation connection unit 10 defines a peripheral rim or flange 10b to which is secured a rubber or rubber-like plastic diaphragm 12. Diaphragm 12 is adhesively secured to the flange 10b but is pressed into sealing engagement with the end face of the back plate 5 of the housing of the pressure generating unit of the high frequency oscillating ventilator apparatus shown in U.S. Pat. No. 4,719,910. The periphery 12a of diaphragm 12 functions as a gasket to make a sealed connection with the high frequency oscillating ventilator apparatus, thus defining an enclosed, restricted chamber between diaphragm 12 and the outer face of the diaphragmatically sealed piston 102. The central portion of diaphragm 12 is disposed closely adjacent to or in contact with the outer face of the diaphragmatically sealed piston 102. The vibrations of the diaphragmatically sealed piston 102 are thus transmitted to the diaphragm 12 and, in turn, create pulses of pressured air to be supplied to the patient through a plastic tubular assemblage, not shown, which is fully described and illustrated in said U.S. Pat. No. 4,719,910 and includes means for supplying oxygen or oxygen enriched air to the patient. Diaphragm 12 may be formed with a concave portion 12b near its periphery to allow for its movement. In the preferred embodiment, a concave portion 12b is provided which is of the same dimension and curvature as the concave portion 112 of the diaphragmatically sealed piston to which it is adjacent so that their curved surfaces can fit together and contact each other, rather than oppose each other as depicted in an alternate embodiment shown in FIG. 6. In the lower portion of the patient isolation connection unit 10, a drain unit 10c is molded which provides a connection for a tube 14 leading to a water trap.

Figure 6:
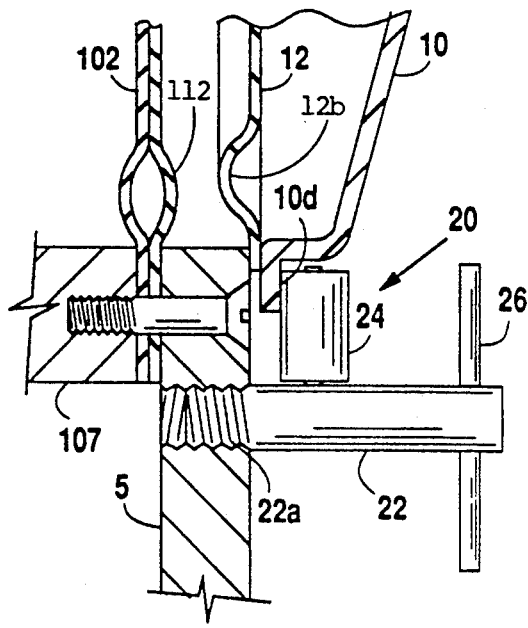
FIG. 6 is an enlarged scale partial sectional view taken on the plane 6—6 of FIG. 5.
Figure 5:
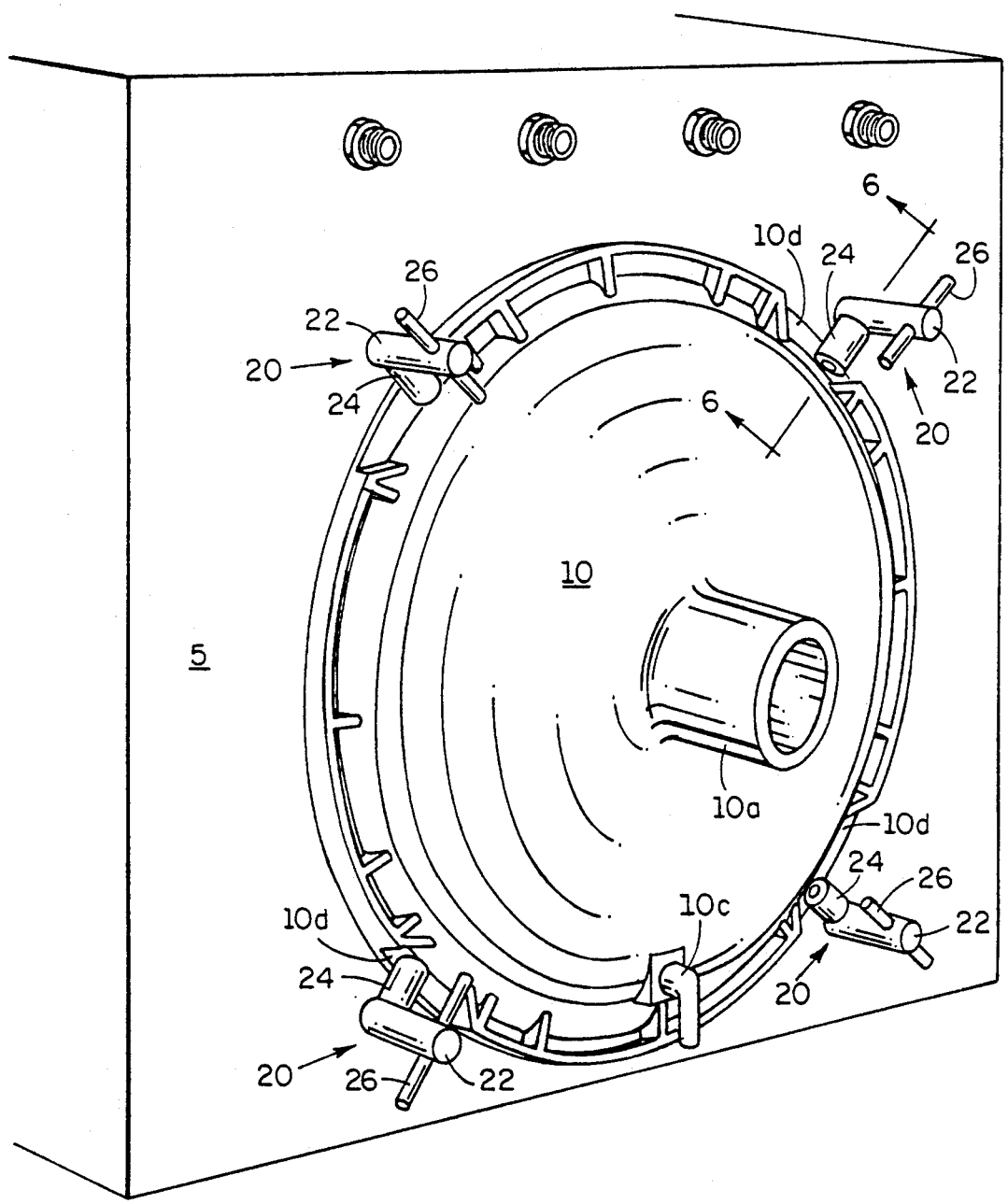
FIG. 5 is a perspective view of the patient isolation apparatus embodying this invention shown in assembled relationship to the housing for the high frequency oscillating ventilator.

Instead of bolting the patient isolation connection unit 10 and attached diaphragm 12 to the back plate 5 of the housing of the high frequency oscillating ventilator, a plurality of peripherally spaced, manually operated clamping units 20 are provided which are best shown in FIGS. 5 and 6. Each clamp 20 comprises a post 22 having a high pitch thread 22a formed on one end and cooperating with threads provided in the base plate element 5. A clamping roller 24 is mounted in radially projecting relationship to a medial portion of each post 22 and is engageable by rotation of the post 22 with a flat cutaway area 10d provided around the periphery of the patient isolation connecting unit 10. Thus, the attachment and removal of the patient isolation connection unit 10 and attached diaphragm 12 to the high frequency oscillating ventilator apparatus may be quickly and easily performed by an approximate 90° rotation of the each post 22. To facilitate the rotation of post 22, a transverse rod 26 may be secured in the outer ends of each post. Other mounting or clamping mechanisms for mounting the patient isolation connection unit 10 and attached diaphragm 12 to the high frequency oscillating ventilator housing may also be utilized.

From the foregoing description, it will be readily apparent that no air which has been in contact with the patient can contact the outer face of the diaphragmatically sealed piston 102, nor enter the interior of the driving apparatus, being blocked by the diaphragm 12. At the same time, the transmission of air pulses to the patient at the desired frequency and with a desired wave form is in no manner hampered. Thus, the main elements of the high frequency oscillating ventilator apparatus may be quickly moved from one patient to another merely by disconnecting the patient isolation connection unit 10 and attached diaphragm 12 used with the first patient, and then replacing such with a new pre-sterilized or pre-disinfected patient isolation assembly.

What is claimed is:

1. A high frequency oscillating ventilator, comprising:
   a source of gas;
   a housing including a magnet and having a diaphragmatically sealed piston mounted therein;
   means conducting the flow of gas from said gas source to the space within said housing on the first side of said piston;
   a coil mounted to the first side of said piston within said housing;
   means in said housing for directing the flow of gas delivered by said gas source to the first side of said piston around said coil and through said housing to the atmosphere, thereby cooling said coil;

means connecting said gas source and the airway of a patient and in adjacent relationship with said diaphragmatically sealed piston but preventing any passage of air which has been in contact with the patient to the space on the second side of said piston; and means for delivering current to said coil operable to reverse the polarity of the current in said coil, thereby causing said coil to move back and forth within said housing relative to said magnet to alternately produce a positive and negative pressure wave in the gas in said connecting means.

2. An oscillating ventilator for air breathing mammalian patients, comprising:

a hollow housing having an open end defined by a peripheral end face concentric about an axis;

a diaphragmatically sealed piston having a periphery sealably closing said open end, said piston having a fixed vibrational axis substantially coaxial with said peripheral end face axis;

electrically actuated means in said housing for vibrating said piston along said fixed axis at a selected frequency and with a selected wave form;

a patient isolation connection means defining an open end chamber having a peripheral rim portion abuttable with said end face;

a flexible diaphragm disc having a peripheral portion sealably secured to said peripheral rim portion and an impermeable medial portion, thereby sealably closing said open end of said chamber;

means for sealably securing said patient isolation connection means to said housing with said medial portion of said diaphragm disc disposed in adjacent relationship to said medial portions of said piston; and tubular means connecting said chamber to the airway of a patient, thereby eliminating contact of said piston with fluids emanating from the patient.

3. An oscillating ventilator for air breathing mammalian patients, comprising:

a housing having an end face defining an opening having a concentric axis;

a diaphragmatically sealed piston having its periphery sealably connected to said end face to close said open end;

electrically actuated means for vibrating said piston along said axis at a selected frequency and with a selected wave form;

patient isolation connection means having one end face sealably connectable with said housing end face around said housing open end;

means on said patient isolation connection means for connecting the interior of said patient isolation connection means with tubing leading to a patient's airway; and a flexible, impermeable diaphragm sealably secured across said one end of said patient isolation means, thereby preventing contact of patient fluids with said piston, said flexible diaphragm being disposed in adjacent relationship to said piston to transmit said vibrations of said piston to the air within said patient isolation connection means.

4. A method of isolating the diaphragmatically sealed piston of an oscillating ventilator from the airways of a patient to be ventilated comprising the steps of:

separating said patient airways from said diaphragmatically sealed piston with an impermeable, flexible diaphragm by (1) locating said impermeable, flexible diaphragm in adjacent relationship with said diaphragmatically sealed piston and (2) ensuring said impermeable, flexible diaphragm vibrates in synchronism with said diaphragmatically sealed piston.

5. A method of modifying an oscillating ventilator comprising the steps of:

providing an oscillating ventilator having a diaphragmatically sealed portion;

separating the airways of a patient from said ventilator by placing an impermeable, flexible diaphragm in adjacent relationship with the diaphragmatically sealed piston of said ventilator and between said patient airways and said ventilator; and ensuring said impermeable, flexible diaphragm vibrates in synchronism with said diaphragmatically sealed piston.

6. A patient isolation apparatus for use with an oscillating ventilator having a diaphragmatically sealed piston mounted within a housing having an open end, comprising:

a patient isolation connection unit having a first opening with a peripheral rim wherein said peripheral rim of said first opening is abuttable to the periphery of said open end of s id ventilator housing, and having a second opening for connection with the airway of a patient;

a flexible, impermeable diaphragm having its periphery sealably attached to said peripheral rim of said first opening of said patient isolation connection unit; and means for removably securing said patient isolation connection unit and attached diaphragm to said open end of said ventilator housing such that said diaphragm is disposed in adjacent relationship to the face of said diaphragmatically sealed piston face.

7. The apparatus defined in claim 6 wherein said patient isolation connection unit comprises a frustoconical shaped annular element having a large end defining said first opening and a smaller opposing end defining a tubing connection means.

8. The apparatus defined in claim 6 wherein said patient isolation connection unit is fabricated from a moldable plastic material.

9. The apparatus of claim 6 further comprising means on said patient isolation connection unit for securing tubing leading to a patient's airway to said second opening.

10. The apparatus defined in claim 6 further comprising latching elements mounted on said ventilator housing around the periphery of said open end of said housing for detachably securing said peripheral rim of said patient isolation connection unit thereto.

11. The apparatus of claim 10 wherein each said latching element comprises a high pitch, internally threaded bore in said ventilator housing;

a mounting bolt having threads engageable with said high pitch, internally threaded bore; and a latch arm secured to said bolt in generally radial relationship thereto and movable by limited rotation of said bolt into clamping engagement with said peripheral rim portion of said patient isolation connection unit.

12. The apparatus of claim 6 further comprising manually actuable latching elements for securing said patient isolation apparatus to said open end of said ventilator housing.

13. The apparatus of claim 6 further comprising a fluid drain extending through and communicating with both sides of said patient isolation connection unit.

* * * * *